US010876136B2

(12) United States Patent
Kalathil et al.

(10) Patent No.: US 10,876,136 B2
(45) Date of Patent: Dec. 29, 2020

(54) METHOD OF PRODUCING ELECTRICALLY ACTIVE BACTERIA REDUCED GRAPHENE OXIDE AND ELECTRICALLY ACTIVE BACTERIA REDUCED GRAPHENE OXIDE

(71) Applicant: KING ABDULLAH UNIVERSITY OF SCIENCE AND TECHNOLOGY, Thuwal (SA)

(72) Inventors: Shafeer Kalathil, Thuwal (SA); Krishna Prasad Katuri, Thuwal (SA); Amira Salman Alazmi, Thuwal (SA); Pedro Miguel Costa, Thuwal (SA); Pascal E. Saikaly, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 699 days.

(21) Appl. No.: 15/626,584

(22) Filed: Jun. 19, 2017

(65) Prior Publication Data
US 2018/0346935 A1 Dec. 6, 2018

Related U.S. Application Data

(60) Provisional application No. 62/512,485, filed on May 30, 2017.

(51) Int. Cl.
*C12P 3/00* (2006.01)
*C01B 32/192* (2017.01)

(52) U.S. Cl.
CPC .............. *C12P 3/00* (2013.01); *C01B 32/192* (2017.08)

(58) Field of Classification Search
CPC ....... C12P 3/00; C01B 32/192; C01B 32/182; C01B 32/198; C01B 2204/00; C01B 2204/02; C01B 2204/04; C01B 2204/06; C01B 2204/065; C01B 2204/20; C01B 2204/22; C01B 2204/24; C01B 2204/26; C01B 2204/28; C01B 2204/30; C01B 2204/32; C01B 32/20; C01B 32/205; C01B 32/21; C01B 32/215; C01B 32/22; C01B 32/225; C01B 32/23
See application file for complete search history.

(56) References Cited

U.S. PATENT DOCUMENTS

2013/0040283 A1* 2/2013 Star .................... G01N 27/127
435/5

OTHER PUBLICATIONS

Salas, et al., Reduction of Graphene Oxide via Bacterial Respiration, ACS Nano 2010; 4(8): 4852-4856 (Year: 2010).*
Akhavan, et al., Toxicity of Graphene and Graphene Oxide Nanowalls Against Bacteria, ACS Nano 2010; 4(10): 5731-5736 (Year: 2010).*

(Continued)

*Primary Examiner* — Daniel C. McCracken
(74) *Attorney, Agent, or Firm* — Pabst Patent Group LLP (57) ABSTRACT

Reduced graphene oxide is produced by adding graphene oxide and electrically active bacteria to a container. After a period of time reduced graphene oxide is produced by an interaction of the electrically active bacteria and the graphene oxide. The resulting composition of matter includes reduced graphene oxide and electrically active bacteria. The resulting composition of matter can be doped with a plurality of different elements.

18 Claims, 11 Drawing Sheets

(56) References Cited

OTHER PUBLICATIONS

Bo, Z., et al., "Green Preparation of Reduced Graphene Oxide for Sensing and Energy Storage Applications", Scientific Reports, Apr. 15, 2014, 4:4684, pp. 1-8.
Bond, D.R., et al., "Electricity Production by Geobacter Sulfurreducens Attached to Electrodes", Applied and Environmental Microbiology, Mar. 2003, vol. 69, No. 3, pp. 1548-1555.
Busalmen, J.P., et al., "C-Type Cytochromes Wire Electricity-Producing Bacteria to Electrodes", Angewandte Chemie International Edition, 2008, 47, pp. 4952-4955.
Chen, S., et al., "Paper-Based N-Doped Carbon Films for Enhanced Oxygen Evolution Electrocatalysis," Advanced Science, 2015, 2, 1400015, pp. 1-5.
Gildemyn, S., et al., "Integrated Production, Extraction, and Concentration of Acetic Acid from CO2 through Microbial Electrosynthesis", Environmental Science & Technology Letters, 2015, 2, pp. 325-328.
Holmes, D.E., et al. "Genes for Two Multicopper Proteins Required for Fe(III) Oxide Reduction in Geobacter sulfurreducens Have Different Expression Patterns Both in the Subsurface and on Energy-Harvesting Electrodes", Microbiology, 2008, 154, pp. 1422-1435.
Kalathil, S., et al., "Nanotechnology to Rescue Bacterial Bidirectional Extracellular Electron Transfer in Bioelectrochemical Systems", RSC Advances, Mar. 17, 2016, 6, pp. 1-49.
Lai, J., et al., "Unprecedented Metal-Free 3D Porous Carbonaceous Electrodes for Full Water Splitting", Energy & Environmental Science, Jan. 20, 2016, 9, pp. 1210-1214.
Li, X., et al., "Simultaneous Nitrogen Doping and Reduction of Graphene Oxide", Journal American Chemical Society, 2009, 131, pp. 1-23.
Liang, Y., et., et al., "Co3O4 Nanocrystals on Graphene as a Synergistic Catalyst for Oxygen Reduction Reaction", Nature Matters, Aug. 7, 2011, 10, pp. 780-786.
Malvankar, N.S., et al., "Microbial Nanowires for Bioenergy Applications", Current Opinion in Biotechnology, 2014, 27, pp. 88-95.
Man, I.C., et al., "Universality in Oxygen Evolution Electrocatalysis on Oxide Surfaces", ChemCatChem, 2011, vol. 3, No. 7, pp. 1159-1165.
Methé, B.A., et al., "Genome of Geobacter Sulfurreducens: Metal Reduction in Subsurface Environments", Science, Dec. 12, 2003, vol. 302, pp. 1967-1969.
Mukherjee, S., et al., "A Biosynthetic Model of Cytochrome C Oxidase as an Electrocatalyst for Oxygen Reduction", Nature Communications, Oct. 12, 2015, 6, pp. 1-9.
Rabaey, K., et al., "Microbial Electrosynthesis—Revisiting the Electrical Route for Microbial Production", Nature, Reviews, Microbiology, Oct. 2010, vol. 8, pp. 706-716.
Wang, D., et al., "Reduced Graphene Oxide-NiO/Ni Nanomembranes as Oxygen Evolution Reaction Electrocatalysts", ECS Journal of Solid State Science and Technology, 2017, 6, pp. M3049-M3054.
Wang, H., et al., "Review on Recent Progress in Nitrogen-Doped Graphene: Synthesis, Characterization, and its Potential Applications", ACS Catalysis, 2012, 2, pp. 781-794.
Wang, J., et al., "Magnesiothermic Synthesis of Sulfur-Doped Graphene as an Efficient Metal-Free Electrocatalyst for Oxygen Reduction", Scientific Reports, Mar. 20, 2015, 5, 9304, pp. 1-9.
Wang, Y., et al., "Nitrogen-Doped Graphene and Its Application in Electrochemical Biosensing", ACS Nano, Apr. 7, 2010, vol. 4, No. 4, pp. 1790-1798.
Wu, J., et al., "Co3O4 Nanocrystals on Single-Walled Carbon Nanotubes as a Highly Efficient Oxygen-Evolving Catalyst", Nano Research, Aug. 2012, vol. 5, Issue 8, pp. 521-530.
Yan, W., et al., "Nitrogen/Sulfur Dual-Doped 3D Reduced Graphene Oxide Networks Supported CoFe2O4 with Enhanced Electrocatalytic Activities for Oxygen Reduction and Evolution Reactions", Carbon, 2016, 99, pp. 195-202.
Youngblood, W.J., et al., "Photoassisted Overall Water Splitting in a Visible Light-Absorbing Dye-Sensitized Photoelectrochemical Cell", Journal of the American Chemical Society, Oct. 8, 2009, 131, pp. 926-927.
Zhang, J., et al., "A Metal-Free Bifunctional Electrocatalyst for Oxygen Reduction and Oxygen Evolution Reactions", Nature Nanotechnology, Apr. 6, 2015, vol. 10, pp. 444-452.
Zhao, Y., et al., "Nitrogen-Doped Carbon Nanomaterials as Non-Metal Electrocatalysts for Water Oxidation", Nature Communications, Aug. 27, 2013, 4:2390, pp. 1-7.

\* cited by examiner

METHOD OF PRODUCING ELECTRICALLY ACTIVE BACTERIA REDUCED GRAPHENE OXIDE AND ELECTRICALLY ACTIVE BACTERIA REDUCED GRAPHENE OXIDE

CROSS-REFERENCE TO RELATED APPLICATIONS

This application claims priority and benefit from U.S. Provisional Patent Application No. 62/512,485, filed on May 30, 2017, the entire disclosure of which is incorporated herein by reference.

BACKGROUND

Technical Field

Embodiments of the subject matter disclosed herein generally relate to reduced graphene oxide and, more particularly, to methods of producing reduced graphene oxide using electrically active bacteria and to a composition of electrically active bacteria reduced graphene oxide.

Discussion of the Background

Graphene (G) has unique structural properties making it particularly promising for use in electrocatalysis, electrode fabrication, and supercapacitors (which can be used for energy storage). In these applications, graphene oxide (GO) is converted into reduced graphene oxide by one of chemical reduction, thermal reduction, hydrothermal reduction, and electrochemical conversion. These reduction techniques suffer from a number of deficiencies. Thermal reduction involves temperatures of approximately 900° C., which is extremely hot and requires a significant energy input to reach and maintain the high temperatures. Chemical reduction typically involves toxic and carcinogenic chemicals, such as hydrazine. Hydrothermal reduction involves the use of an autoclave, which is susceptible to explosions in which pressure and heat rapidly escape the chamber. Electrochemical reduction suffers from low reduction yields and also employs high potentials that can result in non-intentional hydrogen generation, which creates dangerous conditions.

The catalytic performance of virgin graphene or reduced graphene oxide is poor, and the graphene or reduced graphene oxide is typically tailored to create active catalytic sites by doping. Doping can be done at either a pre-production stage of a post-production stage. Conventional graphene doping techniques are expensive, require complicated procedures (e.g., high temperatures and the use of gasses), and use toxic precursors. It should be understood that in this context doping is not merely related to substitution of the carbon atoms in the graphene lattice but also includes intercalation of other elements or substances in the pore channels, in the space between graphene layers and physical/chemical surface sorption.

Accordingly, there is a need for producing doped, reduced graphene oxide at a lower cost, using less complex procedures, and avoiding the use of toxic chemicals.

SUMMARY

According to an embodiment, there is a method of producing reduced graphene oxide. The method involves adding graphene oxide and electrically active bacteria to a container. Reduced graphene oxide is produced a period of time after both the graphene oxide and electrically active bacteria are added to the container by an interaction of the electrically active bacteria and the graphene oxide.

According to another embodiment, there is a composition of matter that includes reduced graphene oxide and electrically active bacteria.

According to yet another embodiment, there is a composition of matter that includes reduced graphene oxide doped with a plurality of different elements.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of reduced graphene oxide.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
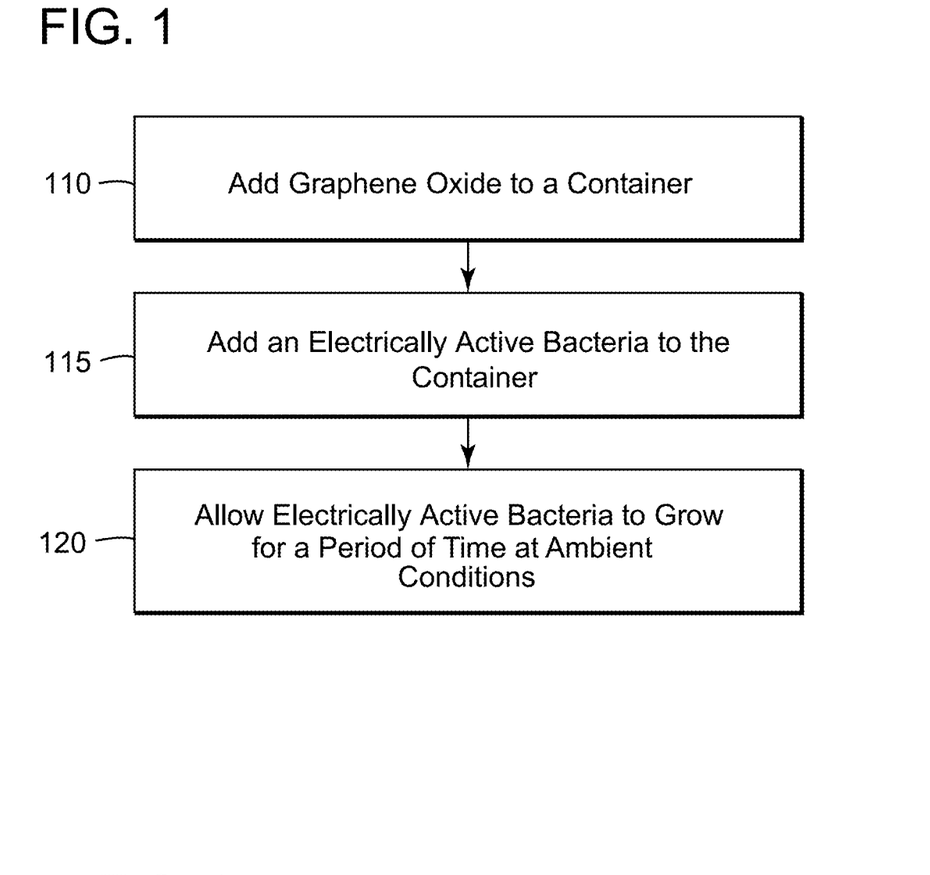
FIG. 1 illustrates a flowchart of a method for producing reduced graphene oxide according to an embodiment.
Figure 2:
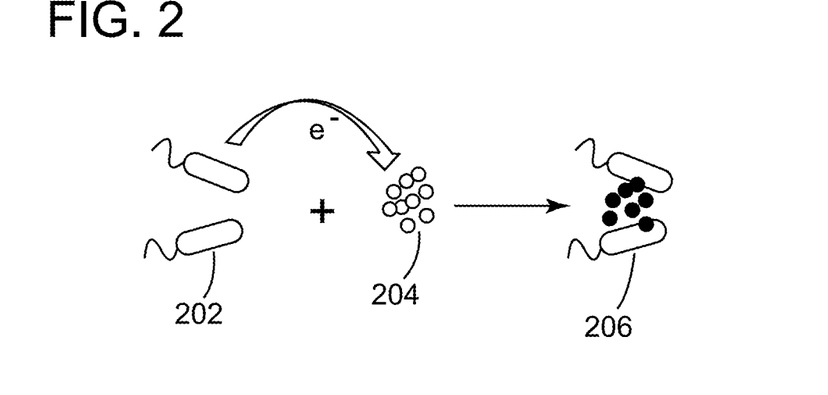
FIG. 2 is a schematic diagram of a method for producing reduced graphene oxide according to an embodiment.

According to an embodiment, reduced graphene oxide is produced using electrically active bacteria under ambient conditions. Specifically, referring to FIGS. 1 and 2, graphene oxide 204 is added to a container (step 110). The graphene oxide can be produced in any manner, including the classical Hummers' method (commonly referred to as HGO) and the improved Hummer's method (commonly referred to as (IGO). Electrically active bacteria 202 is then added to the container (step 115). The electrically active bacteria is allowed to grow for a period of time under ambient conditions to produce reduced graphene oxide 206 that includes the electrically active bacteria (step 120). Specifically, while the electrically active bacteria grow, it interacts with the graphene oxide to reduce it.

Those skilled in the art will recognize that electrically active bacteria are bacteria capable of extracellular electron transfer (EET), which involves molecular mechanisms by which the bacteria transfers electrons across the outer membrane to exchange electrons with extracellular minerals. An example of an electrically active bacteria is *Geobacter sulfurreducens*, which will be used in the examples described below. *Geobacter sulfurreducens* is a gram-negative metal and sulphur reducing bacterium. This bacterium can transfer metabolically generated electrons to external substances/bodies acting as electron acceptors. These include metal oxides and charged electrodes and the transfer process is known as extracellular electron transport. These examples are non-limiting, and therefore the discussion applies to any type of electrically active bacteria/archaea.

Figure 3A:
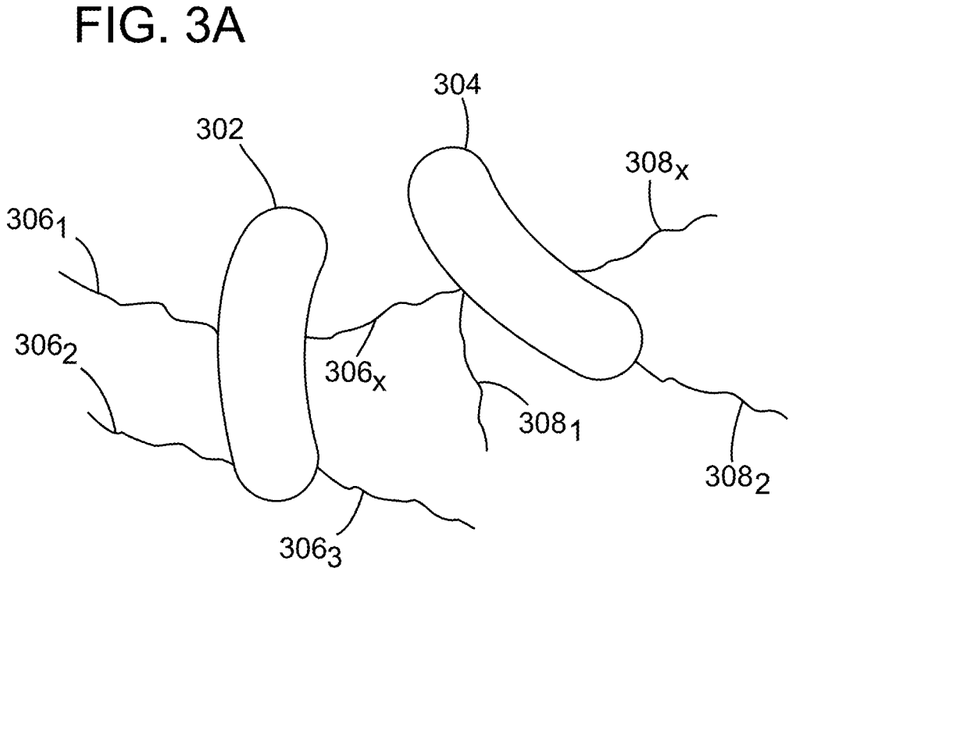
FIG. 3A is a schematic diagram of *Geobacter sulfurreducens* with nano-filaments according to an embodiment.
Figure 3B:
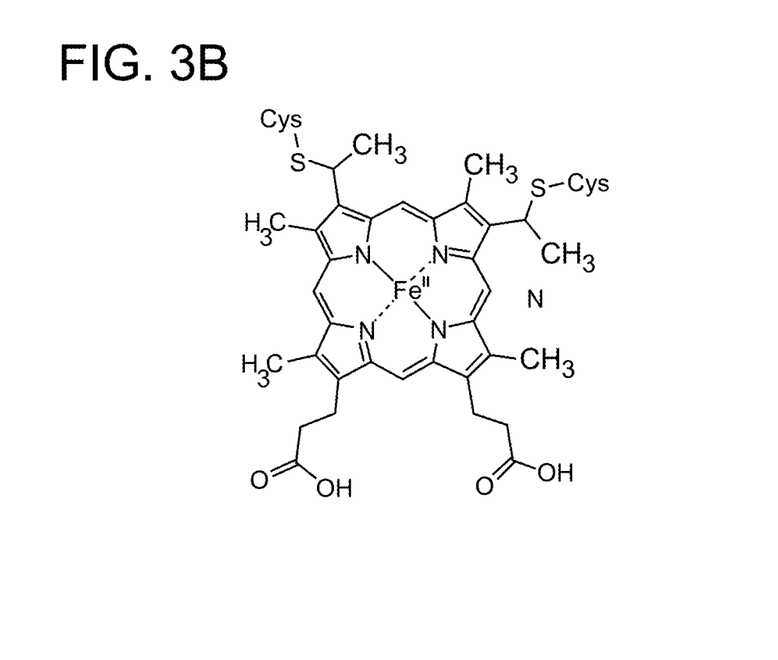
FIG. 3B is a schematic diagram of a typical structure of outer-membrane c-type cytochromes (OM c-Cyts) of *Geobacter sulfurreducens* according to an embodiment.

*Geobacter sulfurreducens* is particularly unique because it possesses multi-heme containing OM c-Cyts and nanofilaments (known as microbial protein nanowires). For example, as illustrated in FIG. 3A, *Geobacter sulfurreducens* 302 and 304 each respectively include one or more nanowires $306_1$-$306_x$ and $308_1$-$308_x$. Further, as illustrated by the structure of OM c-Cyts of *Geobacter sulfurreducens* in FIG. 3B, it contains Fe-porphyrin rings. Additionally, *Geobacter sulfurreducens* is a non-pathogenic microorganism belonging to biosafety level 1, which includes materials that do not cause disease in healthy humans. Thus, unlike conventional graphene oxide techniques that involve toxic chemicals or high temperature or explosive materials, the use of *Geobacter sulfurreducens* is particularly advantageous because it avoids the use of these dangerous materials of conventional reduction techniques. Additionally, *Geobacter sulfurreducens* is easily obtained because it is typically available in nature, such as sediment, wastewaters, anaerobic sludge, etc.

Prior to the reduction process, the *Geobacter sulfurreducens* can be cultured anaerobically using sterile growth medium 141 (German collection of microorganisms and cell cultures, Germany) containing acetate (20 mM; as electron donor) and fumarate (80 mM; as electron acceptor), as previously reported (Okamoto et al. 2014). After two days of anaerobic incubation at room temperature, bacterial cells can be collected by centrifugation and then washed by a sterile growth medium lacking fumarate.

A variety of different strains of *Geobacter sulfurreducens* can be employed for the graphene oxide reduction, such as, for example, strain BEST, KN400 strain, Pili mutant of KN400 strain, etc. Strain BEST is a strain of *Geobacter sulfurreducens* in which the genes for four of the most abundant outer-membrane c-type cytochromes (OmcB, OmcE, OmcS and OmcT) have been deleted. KN400 strain is the most pili (microbial nanowires) producing strain of *Geobacter sulfurreducens*. The Pili mutant of KN400 strain of *Geobacter sulfurreducens* cannot produce protein nanowires, and depending upon the role of excess nanowires in the reduction process, may not be an optimum strain to employ.

Figure 4:
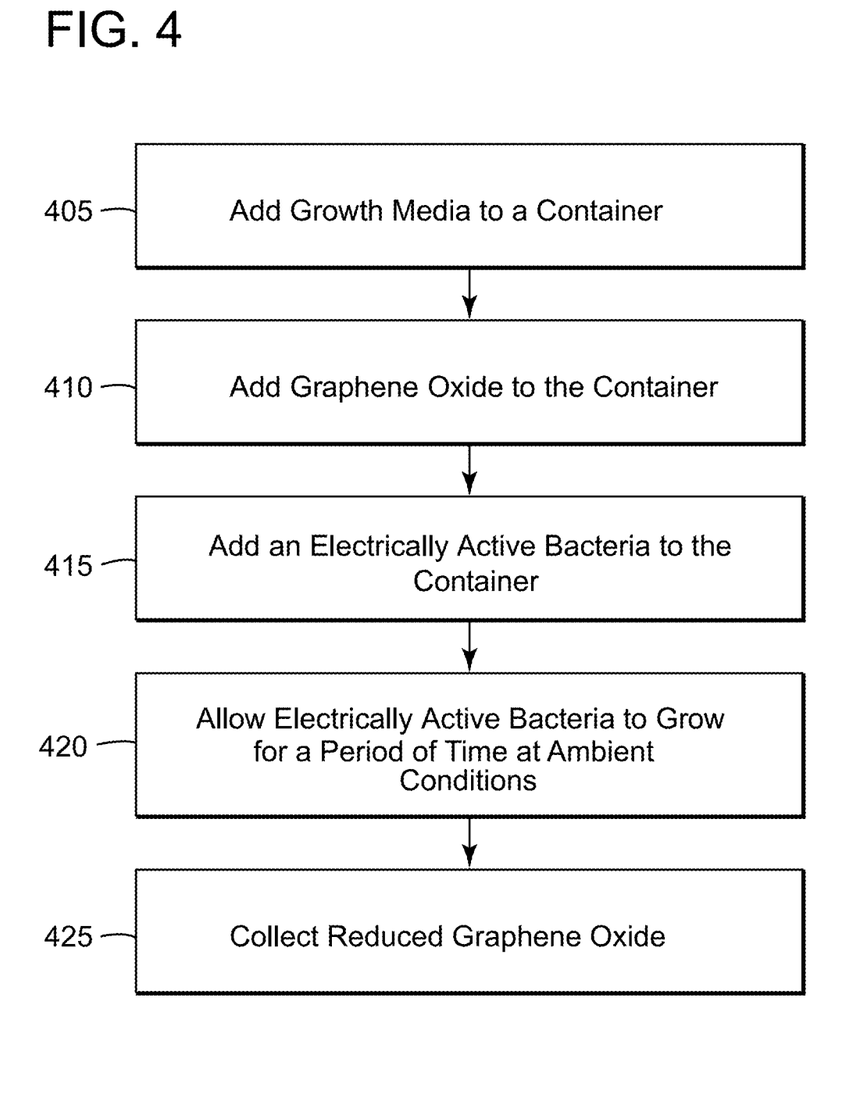
FIG. 4 illustrates a flowchart of a method for producing reduced graphene oxide according to an embodiment.
Figure 5A:
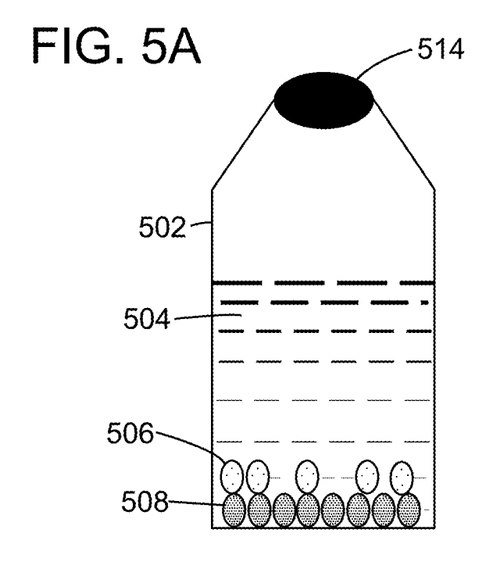
FIGS. 5A and 5B are schematic diagrams of a method of producing reduced graphene oxide according to an embodiment.
Figure 5B:
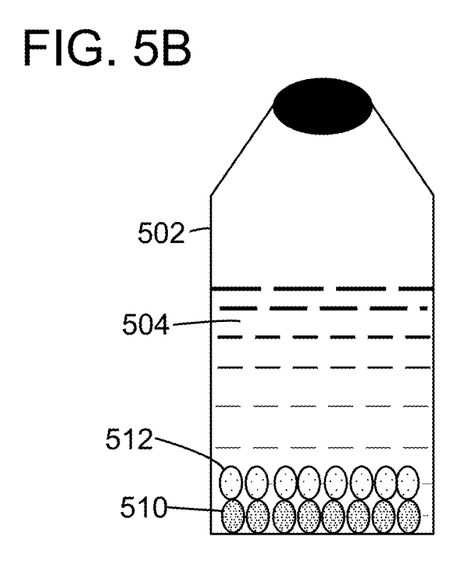

FIGS. 4, 5A, and 5B are a flowchart and schematic diagrams of a method for producing reduced graphene oxide (rGO) according to an embodiment. Initially, a growth media 504 is added to a container 502 (step 405). The amount and type of growth media employed can vary depending upon implementation but can include, in one example, 20 mM of acetate. The growth media includes an electron donor substrate used as part of the reduction process. Electron donor substrates that can be used as a growth media for electrically active bacteria include acetate, formate, $H_2$, volatile fatty acids, and the like. The growth media does not include an electron acceptor because the graphene oxide acts as the electron receptor.

Graphene oxide 508 is then added to the container 502 (step 410). Although the concentration of the graphene oxide added can vary depending upon implementation, in one example, the graphene oxide can have a concentration of 0.4 mg/mL. Electrically active bacteria 506 is then added to the container 502 (step 415). A seal 514 is placed on the container and the electrically active bacteria is allowed to grow for a period of time at ambient conditions so as to form the reduced graphene oxide rGO 510 (step 420). Although ambient conditions can vary, the reduction can take place at, for example, 30° C. and atmospheric pressure. The period of time employed for the reduction process can vary, but in one example, can be two days. The container 502 can be maintained so as to avoid shaking during this period.

After the reduced graphene oxide 510 has been produced it is collected from the container 502 (step 425). The collection of reduced graphene oxide can include centrifugation (e.g., at 8000 rpm for 6 minutes) to obtain the reduced graphene oxide followed by a washing to remove media contribution on the reduced graphene oxide. For example, the material can be washed three times with MilliQ water (vortexing). After washing the material can be dried, such as by placing it in an oven at, for example, 45° C. and maintained there for several hours, such as overnight.

Figure 6:
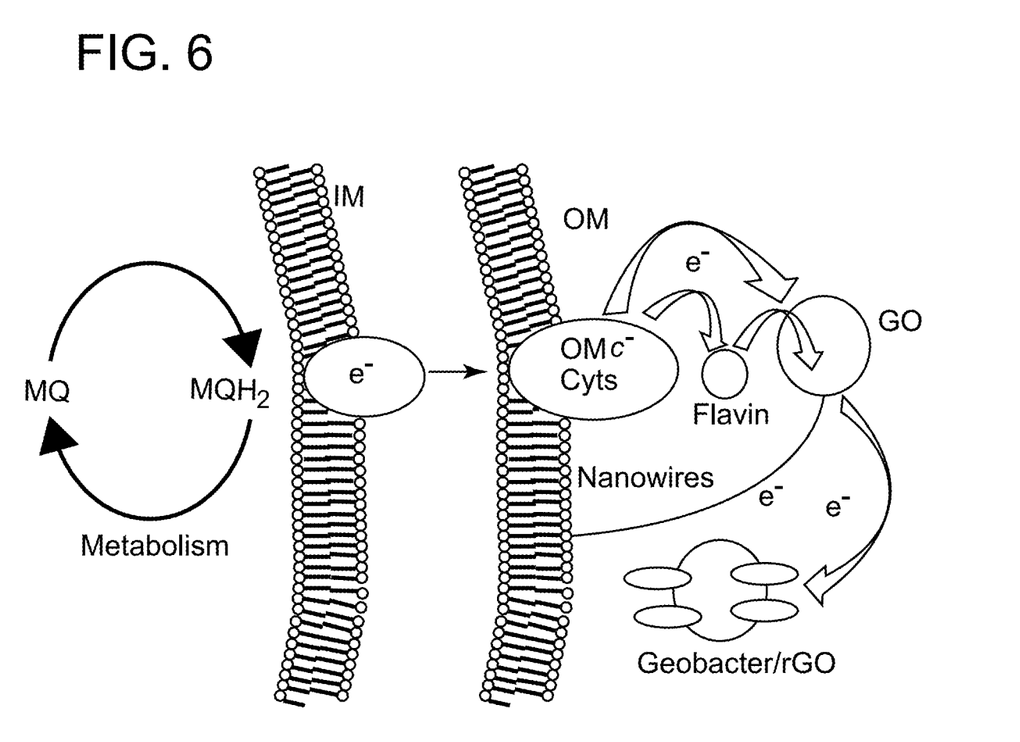
FIG. 6 is a schematic diagram of a possible mechanism for producing reduced graphene oxide using electrically active bacteria.

FIG. 6 is a schematic diagram of a possible mechanism for producing reduced graphene oxide using electrically active bacteria, which in this example is *Geobacter sulfurreducens*. As illustrated, *Geobacter sulfurreducens* includes nanofilaments (also referred to as microbial protein nanowires), and, as discussed above, OM c-Cyts. The OM c-Cyts behave as pseudocapacitors and the microbial nanowires exhibit metal-like electrical conductivity, similar to conducting polymers.

When exposed to the growth media, *Geobacter sulfurreducens* oxidizes the substrate, which causes electrons to move from the inner membrane (IM) to the outer membrane (OM). During its metabolism, *Geobacter sulfurreducens* secrets Flavin, which is supplied with electrons from the outer membrane c-type cytochromes. Flavin is an excellent biocatalyst for various reactions such as oxygen reduction and hydrogen evolution. The outer membrane c-type cytochromes also supplies electrons to the graphene oxide, which forms the *Geobacter sulfurreducens* reduced graphene oxide (*Geobacter*/rGO). Further, nanowires of the outer membrane also supply electrons to the graphene oxide to form the reduced graphene oxide. The reduced graphene oxide includes some *Geobacter sulfurreducens*, which is why it is labeled *Geobacter*/rGO in the figure. The rGO produced by *Geobacter* is expected to exhibit outstanding electrocatalytic and supercapacitance behavior due to the combined presence of OM c-Cyts (which has very good capacitance properties), cell-secreted flavin (secreted during the metabolism of the *Geobacter*) and the protein nanowires (which have very good conduction properties).

Figure 7A:
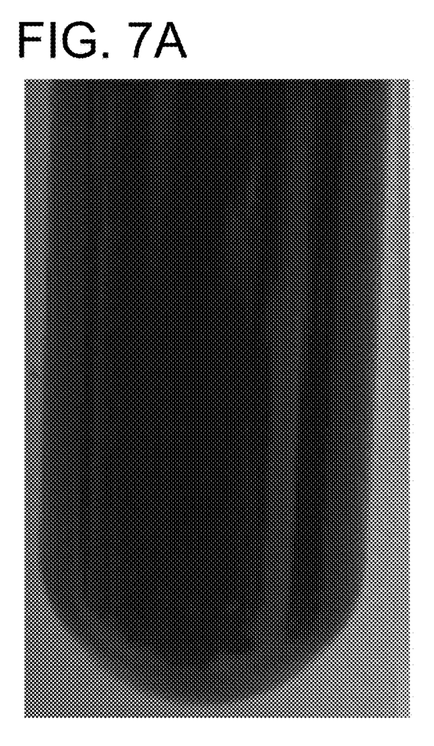
FIGS. 7A and 7B are images a solution of graphene oxide and *Geobacter sulfurreducens* when they are first combined and after a time period of incubation, respectively, according to an embodiment.
Figure 7B:
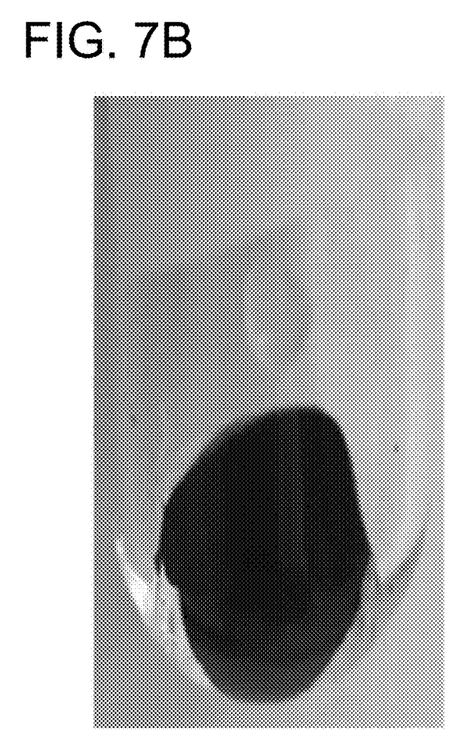

FIGS. 7A and 7B are images of a solution of graphene oxide and *Geobacter sulfurreducens* when they are first combined and after a time period of growth, respectively, according to an embodiment. As illustrated, when graphene oxide and *Geobacter sulfurreducens* are first combined (FIG. 4A), the two have not yet interacted in any significant way, whereas after a period of growth time, the two combine into a dark colored hydrogel precipitated at the bottom of the container.

Figure 7C:
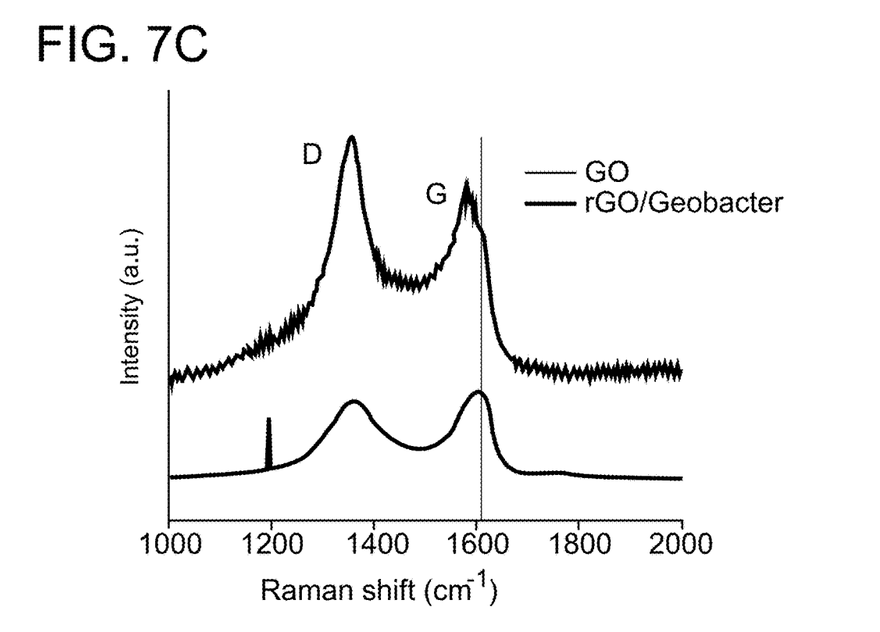
FIG. 7C is a graph of the Raman spectra for graphene oxide and *Geobacter sulfurreducens* reduced graphene oxide according to an embodiment.

FIG. 7C is a graph of the Raman spectra for graphene oxide and *Geobacter sulfurreducens* reduced graphene oxide according to an embodiment in which the upper curve represents graphene oxide reduced with *Geobacter sulfurreducens* and the lower curve represents regular graphene oxide. The spectra shows the presence of the D and G band characteristic of these carbon materials before and after the reduction procedure. Production of the graphene oxide is confirmed by the shift of the G band after reduction of the graphene oxide (as indicated by the vertical line) and the increase of the D band intensity.

One application for reduced graphene oxide is water splitting, which is the separation of water into oxygen and hydrogen, which is a key process for solar cells, metal-air batteries, and microbial electrosynthesis. In order to determine the suitability of the *Geobacter sulfurreducens* reduced graphene oxide for water splitting, the tendency of the reduced graphene oxide towards oxygen evolution reaction (OER), which is a type of water splitting electrocatalysis, is evaluated by subjecting the *Geobacter sulfurreducens* reduced graphene oxide to 22 hours of chronoamperometry during which it was examined. This testing involved a rotating disc electrode (RDE).

The working electrode was prepared by dispersing the graphene oxide reduced by *Geobacter sulfurreducens* (~2 mg) in 500 µl of ethanol, 500 µl of water and 15 µl of Nafion solution (as binder). The dispersed solution was sonicated for 30 min. Next, 2 µl of the obtained slurry was drop-coated onto a 3 mm glassy carbon disc electrode (GCE; loading concentration ~0.049 mg/cm$^2$) and dried under a lamp for 1 hour. The electrochemical measurement performed using a BioLogic VMP3 electrochemical working station in 1 M KOH (Sigma Aldrich, semiconductor grade, pellets, 99.99% trace metals basis) at room temperature using a three-electrodes system, in which Pt wire and Mercury/Mercury oxide reference electrode (Hg/HgO) (1 M NaOH) were used as counter and reference electrodes, respectively. Linear sweep voltammetry (LSV) experiments were performed at a scan rate of 10 mV/S while maintaining a constant rotational speed of 1600 rpm under the nitrogen environment. Electrochemical impedance spectroscopy (EIS) measurements were performed for the *Geobacter*/rGO in 1 M KOH from 1000 kHz to 100 mHz.

Figure 8A:
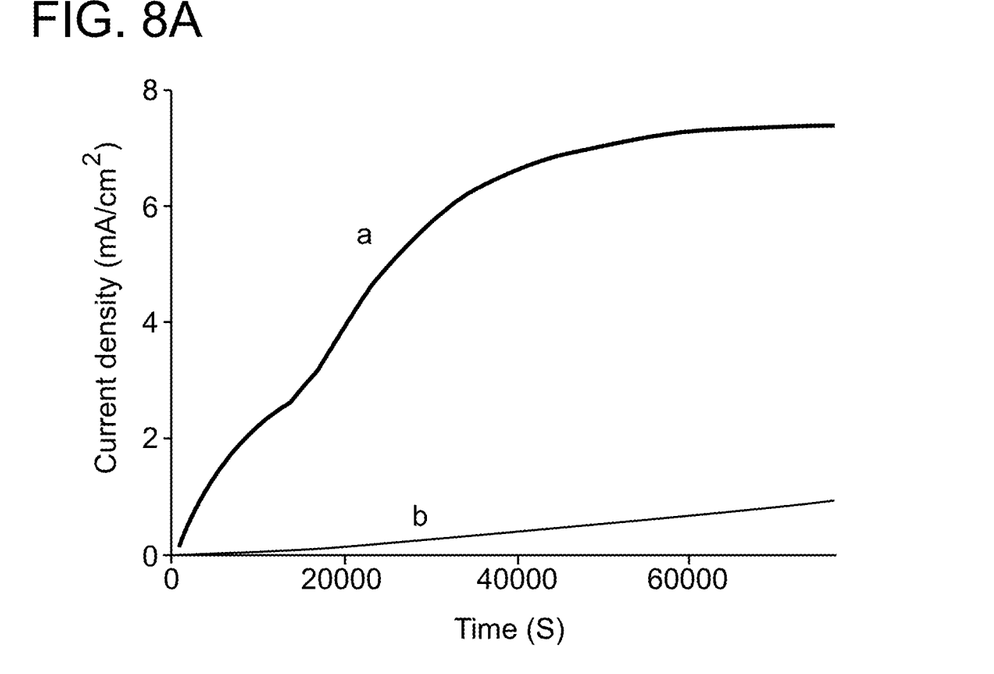
FIGS. 8A and 8B respectively illustrate chronoamperometry (CA) and linear sweep voltammetry (LSV) profiles of *Geobacter sulfurreducens* reduced graphene oxide (a) and hydrothermally reduced graphene oxide (HrGO; b) according to an embodiment.
Figure 8B:
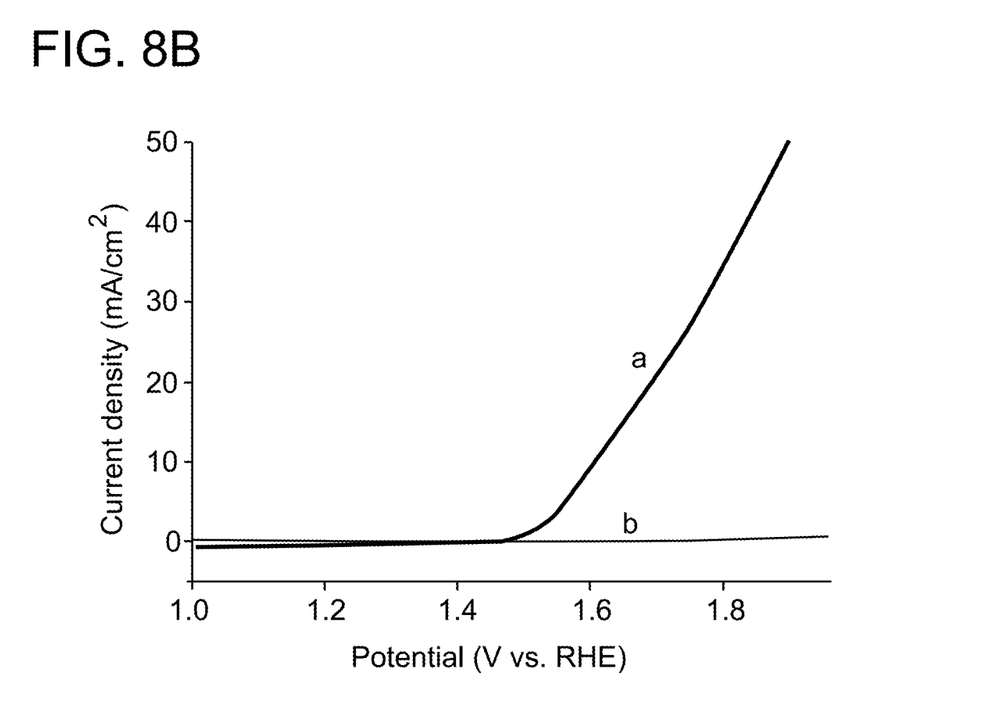

FIGS. 8A and 8B are graphs illustrating measurements of *Geobacter sulfurreducens* reduced graphene oxide (the curve labeled "a" in FIGS. 8A and 8B) and hydrothermally reduced graphene oxide (the curve labeled "b" in FIGS. 8A and 8B). FIG. 8A illustrates plots of the chronoamperometry profile of *Geobacter sulfurreducens* reduced graphene oxide and hydrothermally reduced graphene oxide at an applied potential of 0.8 V versus standard hydrogen electrode (SHE). FIG. 8B illustrates linear sweep voltammetry (LSV) plots of *Geobacter sulfurreducens* reduced graphene oxide and hydrothermally reduced graphene oxide in 1 M KOH solution at 1600 rpm. FIGS. 8A and 8B illustrate that the *Geobacter sulfurreducens* reduced graphene oxide exhibited excellent oxygen evolution reaction, whereas hydrothermally reduced graphene oxide did not demonstrate any oxygen evolution reaction.

In addition to evaluation of the *Geobacter sulfurreducens* reduced graphene oxide towards oxygen evolution reaction, it can also be evaluated of its activity towards oxygen reduction reaction (ORR) and hydrogen evolution reaction (HER), as well as for its supercapacitance capabilities.

Evaluation toward oxygen reduction reaction can employ an RDE. The working electrode can be prepared by dispersing approximately 2 mg of *Geobacter sulfurreducens* reduced graphene oxide in 170 µl of ethanol and then sonicating for 30 minutes. Next, 2 µl of the obtained slurry can be drop-coated onto a glassy carbon electrode (GCE) (3 mm diameter) and dried in an oven and heated at 100° C. under air for 1 hour. The electrochemical measurement can be carried out using, for example, a BioLogic VMP3 electrochemical working station in acid solution 0.05M $H_2SO_4$ (Sigma Aldrich, 99%) or 0.1 M KOH (Sigma Aldrich, 99%) at room temperature using a three-electrodes system, in which carbon/Pt and Ag/AgCl electrode saturated in KCl can be used as counter and reference electrodes, respectively. Cyclic voltammetry (CV) experiments can be performed at a scan rate of 5 mV s$^{-1}$ while maintaining a constant rotational speed of 1600 rpm. Electrochemical impedance spectroscopy (EIS) can be performed for the rGO materials in acid solution (0.05 M $H_2SO_4$) from 1000 kHz to 100 mHz at different ORR over potentials.

Evaluation toward hydrogen evolution reaction can also employ an RDE. The working electrode can be prepared by dispersing approximately 2 mg of the *Geobacter sulfurreducens* reduced graphene oxide in 170 µl of ethanol and then sonicating for 30 minutes. Next, 2 µl of the obtained slurry can be drop-coated onto a glassy carbon electrode (GCE) (3 mm diameter) and dried in an oven and heated at 100° C. under air for 1 hour. The electrochemical measurement can be carried out using, for example, a BioLogic VMP3 electrochemical working station in acid solution 0.05M $H_2SO_4$ (Sigma Aldrich, 99%) or 0.1 M KOH (Sigma Aldrich, 99%) at room temperature using a three-electrodes system, in which carbon/Pt and Ag/AgCl electrode saturated in KCl can be used as counter and reference electrodes, respectively. Cyclic voltammetry (CV) experiments can be performed at a scan rate of 5 mV s$^{-1}$ while maintaining a constant rotational speed of 1600 rpm. Electrochemical impedance spectroscopy (EIS) can be performed for the rGO materials in acid solution (0.05 M $H_2SO_4$) from 1000 kHz to 100 mHz at different HER over potentials.

Supercapacitance evaluation can also involve an RDE. The working electrodes can be prepared by mixing approximately 2 mg of the *Geobacter sulfurreducens* reduced graphene oxide, 15 µl of Nafion, 500 µl water, and 500 µl ethanol. The mixture can then be ultrasonicated for 30 minutes to form a homogenous slurry. The slurry can be drop-cast onto the glassy carbon electrode (3 mm diameter) and dried under a light lamp for ~10 min. All electrochemical experiments can be carried out in 1 M KOH at room temperature using a three-electrode system, in which a Pt wire and a mercury/mercury oxide reference electrode (Hg/HgO) can be used as the counter and reference electrodes, respectively. Cyclic voltammetry (CV) at scan rates 100 mV s$^{-1}$ and galvanostatic charge-discharge assays can be carried out using, for example, a BioLogic VMP3 electrochemical working station. In this case, a supercapacitor may have two electrical conductors made out of the *Geobacter*/rGO and a dielectric material located between the two conductors. Any dielectric material may be used.

For catalysis and supercapacitor electrodes, it is desired that the support's specific surface area is maximized. To achieve this, the rGO post-synthesis drying step needs to be studied. A hydrothermally-reduced GO, when treated with critical point drying, results in a high specific surface area (364 m$^2$ g$^{-1}$) and an advantageous pore volume. Furthermore, when investigating its electrochemical response, it looks superior to the analogous materials dried with vacuum or freeze drying. Therefore, the drying of the final product may involve critical point drying. It is expected that the rGO/*Geobacter*, when dried supercritically, will have more surface area, pore volume and porosity than other rGOs reported in the literature. Moreover, one additional outcome of the drying step is that it should be possible to prevent the collapse of the porous 3D network. This would result in not just a more efficient catalytic system (for hydrogen evolution reaction, HER, and oxygen reduction reaction, ORR), but also one that provides long diffusion channels that enable the electrolyte ion to move more easily into the inner region of the electrode. The latter would have positive implications for energy storage and conversion systems such as supercapacitors and batteries.

An additional advantage of using electrically active bacteria, such as *Geobacter sulfurreducens*, to produce reduced graphene oxide is the elimination of a separate doping step because *Geobacter sulfurreducens* outer membrane contains certain elements (i.e. metal prosthetic groups in c-type cytochromes) that are typically added in a doping step separate from the graphene oxide reduction. Specifically, the doping occurs simultaneously with the production of the electrically active bacteria reduced graphene oxide. Accordingly, the *Geobacter sulfurreducens* reduced graphene oxide was examined before and after chronoamperometry to determine whether the minerals present in the *Geobacter sulfurreducens* prior to reduction of the graphene oxide also exist in the reduced graphene oxide after chronoamperometry.

Figure 9A:
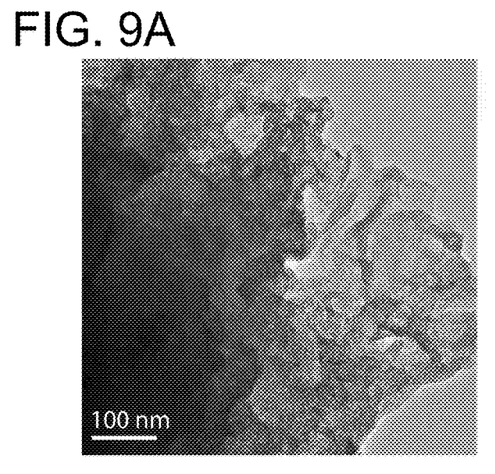
FIGS. 9A-9D are images of *Geobacter sulfurreducens* reduced graphene oxide prior to chronoamperometry analysis according to an embodiment.
Figure 9B:
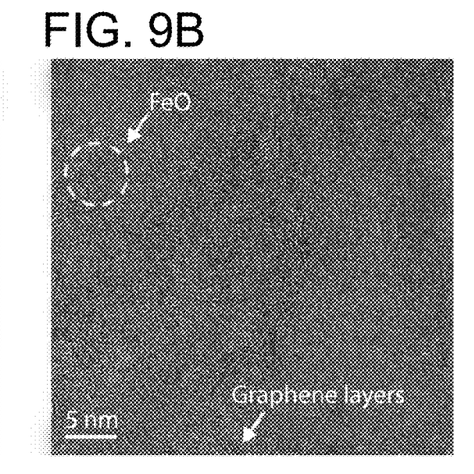
Figure 9C:
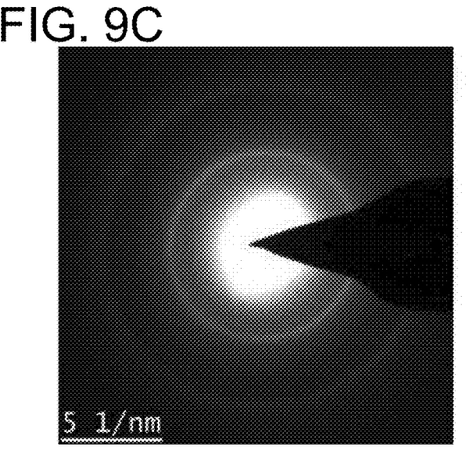
Figure 9D:
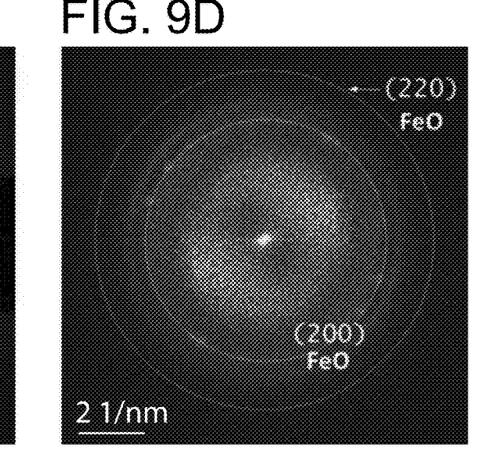
Figure 10A:
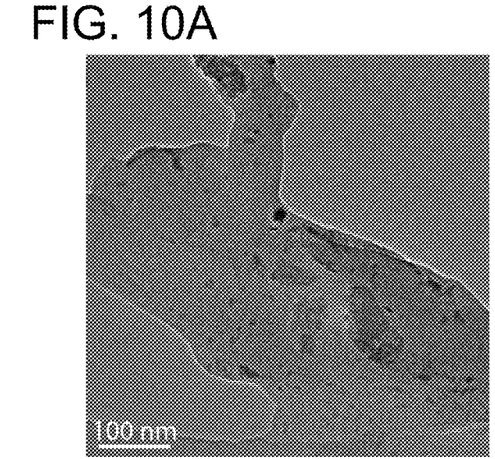
FIGS. 10A-10D are images of *Geobacter sulfurreducens* reduced graphene oxide after chronoamperometry analysis according to an embodiment.
Figure 10B:
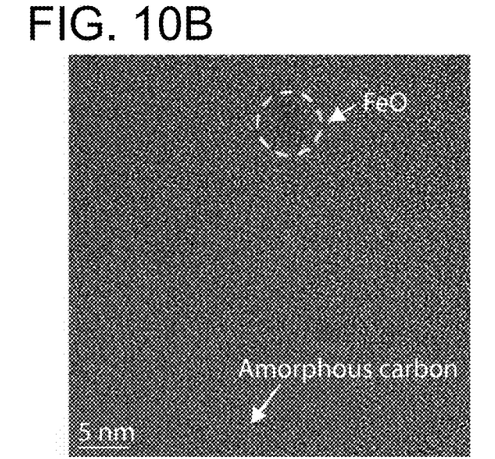
Figure 10C:
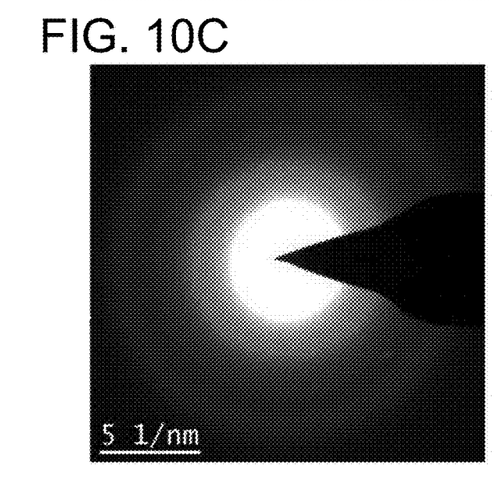
Figure 10D:
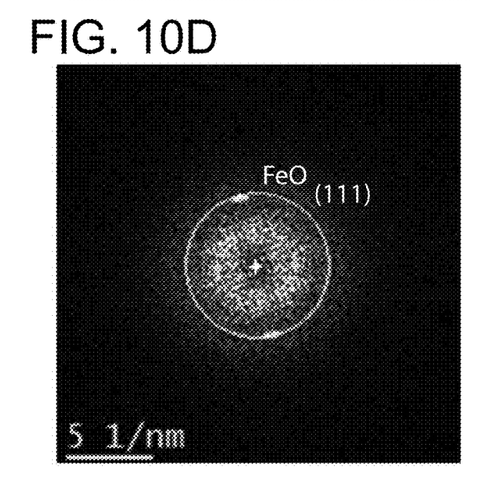

FIGS. 9A-9D are images of *Geobacter sulfurreducens* reduced graphene oxide before chronoamperometry and FIGS. 10A-10D are images of *Geobacter sulfurreducens* reduced graphene oxide after chronoamperometry. Specifically, FIGS. 9A, 9B, 10A, and 10B are transmission electron microscope (TEM) images of the *Geobacter sulfurreducens* reduced graphene oxide; FIGS. 9C and 10C are images of diffraction patterns of selected areas of the *Geobacter sulfurreducens* reduced graphene oxide; and FIGS. 9D and 10D are images of Fast Fourier Transform (FFT) patterns of *Geobacter sulfurreducens* reduced graphene oxide.

As illustrated in FIGS. 9A and 9B, prior to chronoamperometry, the *Geobacter sulfurreducens* reduced graphene oxide contains FeO and graphene layers, whereas FIGS. 10A and 10B show that after chronoamperometry, the *Geobacter sulfurreducens* reduced graphene oxide contains FeO and amorphous carbon. As will be appreciated by comparing FIGS. 9A and 10A, the atomic arrangement of the carbon materials is considerably changed after chronoamperometry compared to prior to chronoamperometry. Specifically, prior to chronoamperometry (FIG. 9A) the *Geobacter sulfurreducens* reduced graphene oxide is more crystalline than after chronoamperometry (FIG. 10A), in which the reduced graphene oxide has lost its cryalline order and become amorphous. The change from crystallinity to amorphous is believed to be beneficial for oxygen evolution reaction.

Regarding FIGS. 9C and 9D respectively show selected area electron diffraction (SAED) pattern and Fast Fourier Transform (FFT) pattern of *Geobacter sulfurreducens* reduced graphene oxide prior to chronoamperometry. As illustrated, these patterns indicate the crystallinity of the reduced graphene oxide.

FIGS. 10C, and 10D respectively show the SEAD pattern and FFT pattern of *Geobacter sulfurreducens* reduced graphene oxide after chronoamperometry. These patterns indicate the amorphous structure of the reduced graphene oxide after the chronoamperometry. Further, FIGS. 9B, 9D, 10B, and 10D illustrate the presence of FeO both before and after chronoamperometry.

Figure 11A:
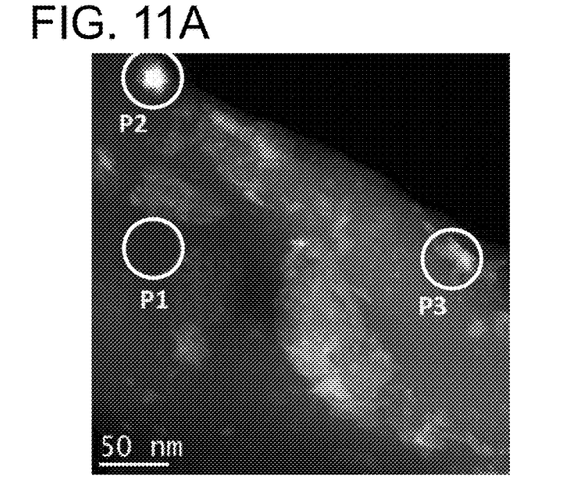
FIGS. 11A-11D are elemental analysis (EDS) of FIGS. 9A-9D *Geobacter sulfurreducens* reduced graphene oxide after chronoamperometry according to an embodiment.
Figure 11B:
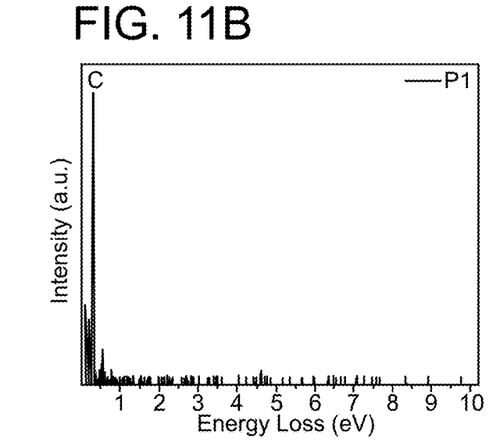
Figure 11C:
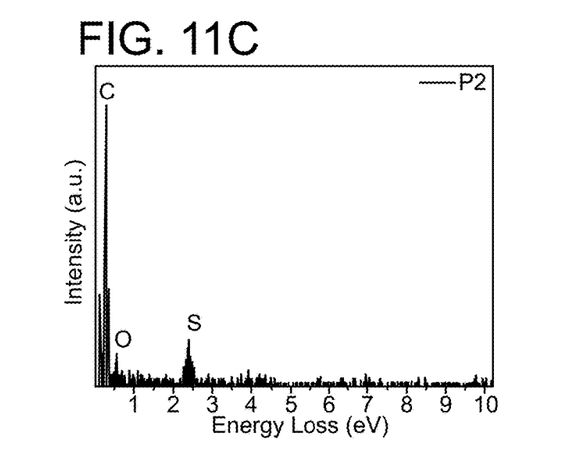
Figure 11D:
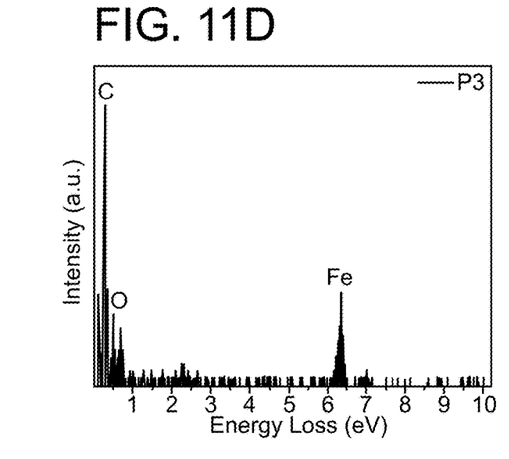

FIG. 11A is a TEM image of *Geobacter sulfurreducens* reduced graphene oxide after chronoamperometry and FIGS. 11B-11D are elemental analysis plots corresponding to the three points (P1-P3) in the TEM image. As illustrated in FIGS. 11B-11D, sulfur (S) and iron (Fe) are present on the surface of the *Geobacter sulfurreducens* reduced graphene oxide after chronoamperometry. Specifically, FIG. 11B illustrates that at point P1 there is carbon (C) and oxygen (O); FIG. 11O illustrates that at point P2 there is carbon, oxygen, and sulfur; and FIG. 11D illustrates that at point P3 there is carbon, oxygen, and iron. It will be recognized that other elements can be present on the surface of the *Geobacter sulfurreducens* reduced graphene oxide that are not detected by this process but can be detected using other processes, such as CHNS analysis, which is a combustion analysis technique. Doping graphene with non-metals (e.g., sulfur, nitrogen, phosphorous, fluorine, and oxygen) and metals (e.g., iron and copper) has been proven to be an effective strategy to make it suitable for electrocatalysis such as oxygen evolution reaction (OER), hydrogen evolution reaction (HER) and oxygen reduction reaction (ORR).

Figure 12:
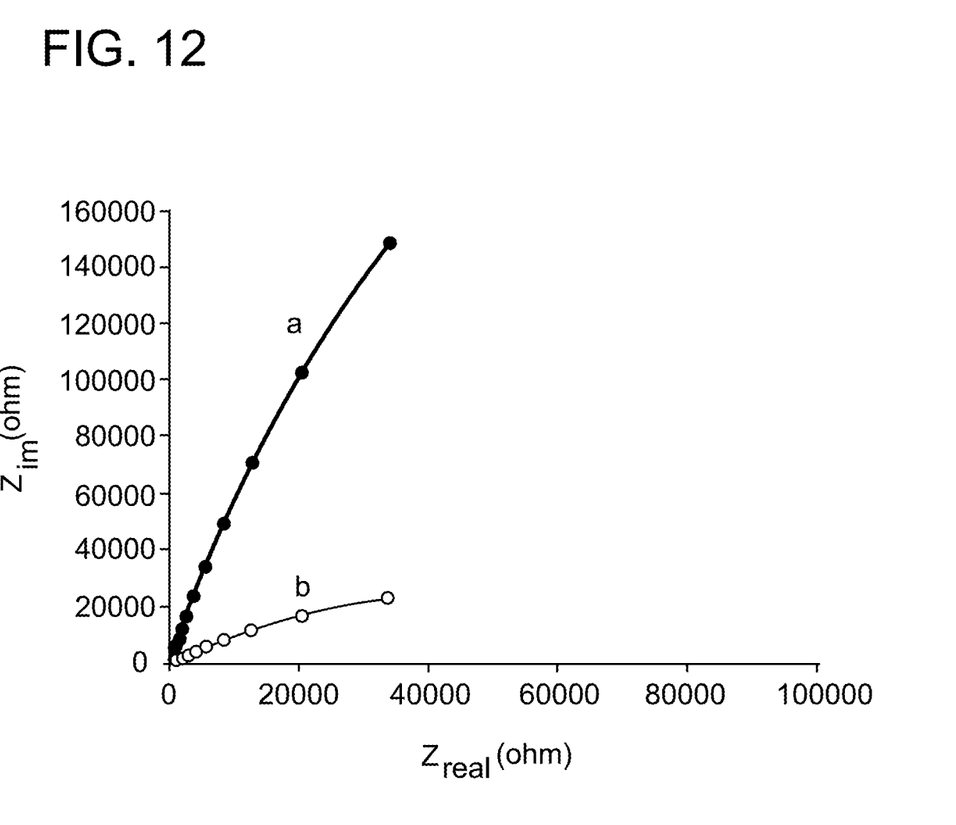
FIG. 12 is a graph of electrochemical impedance spectroscopy (EIS) before and after chronoamperometry analysis according to an embodiment.

FIG. 12 illustrates the electrochemical impedance spectroscopy (EIS) of the *Geobacter sulfurreducens* reduced graphene oxide before chronoamperometry (the curve labeled "b" in the figure) and after chronoamperometry (the curve labeled "a" in the figure). As illustrated, the conductivity of the *Geobacter sulfurreducens* reduced graphene oxide after chronoamperometry is increased. This indicates that more iron is exposed to the reduced graphene oxide surface after the chronoamperometry, which in turn increased the conductivity.

As discussed above, one advantage of the use of electrically active bacteria is it avoids the use of toxic precursors or explosive materials or high temperatures as compared to conventional methods. Table 1 summarizes the precursors used in some conventional graphene oxide reduction processes compared to the use of an electrically active bacteria described herein, as well as the dopant content in each method (N is the nitrogen content; S is the sulfur content; P is the phosphorus content; F is the fluorine content; Fe is the iron content; and Cu is the copper content). Note that the embodiments discussed above are described by the last entry of Table 1. Other than the last entry, the dopant content is the result of a separate doping step performed before or after production of the reduced graphene oxide.

TABLE 1

| Synthesis method | Precursors | Dopant content wt % |
|---|---|---|
| CVD | Cu foil as catalyst, $NH_3$/He | N = 0.34-3.31 |
| CVD | Cu foil as catalyst, pyridine | N = 0.51 |
| Thermal treatment | Graphite oxide after thermal expansion, $NH_3$/Ar | N = 0.23 |
| Thermal treatment | GO, $NH_3$/Ar (10% $NH_3$) | N = 0.64-1.06 |
| Thermal treatment | GO, melamine | N = 1.5-2.11 |
| Plasma treatment | Graphite oxide after thermal expansion, N2 plasma | N = 0.62 |
| Plasma treatment | Chemically synthesized graphene, $N_2$ plasma | N = 0.28 |
| $N_2H_4$ treatment | GO, $N_2H_4$, $NH_3$ | N = 0.85-1.10 |
| CVD | Ni (np-Ni), pyridine, thiophene | N = 0.8, S = 2.36 |
| Thermal treatment | Oxidized graphene foam, thiourea | N = 1.18, S = 0.24 |
| Pyrolysis | Polyaniline-coated GO, ammonium Hexafluorophosphate | N = NA, P = NA, F = NA |
| Thermal treatment | $Na_2CO_3$, $Na_2SO_4$, Magnesium powder | S = 0.85-1.22 |
| Thermal treatment | GO, dimethyl sulfoxide | S = 2.19 |
| Pyrolysis | GO, dopamine, $N_2$ | N = 0.83, S = 2.81 |
| Hydrothermal treatment | GO, CNT, urea, thiourea | N = 0.71, S = 0.34 |
| Thermal treatment | Oxidized carbon cloth, aniline, phytic acid | N = 0.09, P = 0.15 |
| Electrically Active Bacteria | GO, acetate, *Geobacter sulfurreducens*, room temature | N = 9.31, S = 0.1683, P = 0.8212, Fe = 0.0369, Cu = 0.0066 |

The *Geobacter sulfurreducens* reduced graphene oxide showed an overpotential of 0.37 V to reach 10 mA/cm², which as illustrated in Table 2 below, is within the range of other catalysts used for oxygen evolution reaction. Note that the embodiments discussed above are described by the last entry of Table 2.

TABLE 2

| Catalyst | Catalyst amount (mg/cm²) | Electrolyte solution | Potential at 10 mA/cm² (vs. RHE) |
|---|---|---|---|
| Nitrogen doped carbon | 0.2 | 0.1M KOH | 1.61 |
| Nitrogen-Doped Graphene/Carbon Nanotube Hybrids | 0.26 | 0.1M KOH | 1.63 |
| $IrO_2$-CNT | 0.2 | 0.1M KOH | 1.59 |
| $Co_3O_4$/N-graphene | 0.24 | 0.1M KOH | 1.60 |
| $Co_3O_4$/SWNTs | 0.05 | 1M KOH | 1.80 |
| Ni-Nitrogen doped graphene | 0.05 | 0.1M KOH | 1.60 |
| Nitrogen and sulfur codoped graphite foam | NA | 1M KOH | 1.61 |
| Nitrogen, phosphorous, fluorine tridoped graphene | NA | 0.1M KOH | 1.70 |
| 20 wt % Ru/C | 0.028 | 0.1M KOH | 1.62 |
| 20 wt % Pt/C | 0.028 | 0.1M KOH | 1.88 |
| MnO | 0.028 | 0.1M KOH | 1.84 |
| $Mn_2O_3$ | 0.028 | 0.1M KOH | 1.81 |
| rGO-NiO/Ni | 0.24 | 1M KOH | 1.76 |
| Graphitic carbon nitrate (G-$C_3N_4$) | 0.1 | 0.1M KOH | 1.644 |
| IrO2 | 0.1 | 0.1M KOH | 1.74 |
| N, P co-doped graphene | 0.15 | 0.1M KOH | 1.62 |
| N, O dual-doped graphene-CNT | 1.75 | 0.1M KOH | 1.78 |
| *Geobacter sulfurreducens* reduced graphene oxide | 0.049 | 1M KOH | 1.60 |

To better understand the elemental composition of the *Geobacter sulfurreducens* reduced graphene oxide, both pure *Geobacter sulfurreducens* and *Geobacter sulfurreducens* reduced graphene oxide were subjected to inductively coupled plasma optical emission spectrometry (ICP-OES) analysis and carbon, hydrogen, nitrogen, sulphur (CHN—S) analysis, the results of which are respectively illustrated in Tables 3 and 4 below.

TABLE 3

| | Element (ppm) (mg/Kg) | | | |
|---|---|---|---|---|
| Sample | S | P | Fe | Cu |
| Geobacter sulfurreducens | 3957 | 12715 | 733 | 775 |
| Geobacter/rGO | 1683 | 8212 | 369 | 66 |

TABLE 4

| | Element (ppm) (mg/Kg) | | | |
|---|---|---|---|---|
| Sample | wt % N | wt % C | wt % H | wt % S |
| Geobacter sulfurreducens | 12.74 | 45.54 | 6.16 | 0.40 |
| Geobacter/rGO | 9.31 | 46.93 | 4.78 | 0.18 |

These tables demonstrate that the elements present in the pure *Geobacter sulfurreducens* are also present in significant quantities in the *Geobacter sulfurreducens* reduced graphene oxide. Thus, the elements in the pure *Geobacter sulfurreducens* dope the reduced graphene oxide during the reduction process without requiring a separate doping step as in conventional techniques. This is advantageous because sulfur, phosphorus, iron, copper, and nitrogen have been shown to be excellent candidates for oxygen evolution reaction.

The graphene oxide reduced by *Geobacter sulfurreducens* can be prepared using any technique. One example involves oxidizing graphite (G) powder (Alfa Aesar, <50 μm) using the so-called improved-Hummers' method, and then adding 3 g of graphite powder (Alfa Aesar) to a mixture of 360 mL $H_2SO_4$ (Sigma Aldrich, 99%) and 40 mL $H_3PO_4$ (Sigma Aldrich, 85 wt %). This can be followed by the slow addition of 18 g of $KMnO_4$ (Acros, 99%) while maintaining the reaction temperature at <20° C. The resulting suspension can then be heated in an oil bath to 50° C. and stirred for 12 hours. The color of the mixture typically turns from black to mud-brown. The reaction can then be allowed to cool to room temperature and treated with 400 mL of cold deionized water plus 3 mL of $H_2O_2$ (Sigma Aldrich, 30%). The product can be diluted with deionized water to a total volume of 2 L. Finally, the suspension can be repeatedly washed with water and centrifuged (Hettich U320, 9000 rpm, 10 min) until the pH was nearly neutral. The suspension can then be vacuum dried in the centrifuge tubes (60° C., 12 hours) and the resulting powder collected. A graphene oxide (GO) solution (5 mg/ml) can be prepared by dispersing the GO powder in deionized water and then stirring the mixture for 24 hours.

The disclosed embodiments provide methods of producing reduced graphene oxide using an electrically active bacteria and electrically active bacteria reduced graphene oxide. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A composition of matter comprising: reduced graphene oxide; and electrically active bacteria, wherein the electrically active bacteria are *Geobacter sulfurreducens*.

2. The composition of matter of claim 1, wherein the composition of matter is doped with both metal and non-metal elements.

3. The composition of matter of claim 1, wherein portions of the composition of matter are amorphous.

4. The composition of matter of claim 1, comprising *Geobacter sulfurreducens* strain, KN400, or Pili mutant of KN 100.

5. A method of producing the reduced graphene oxide of claim 1, the method comprising:
   adding graphene oxide to a container; and
   adding *Geobacter sulfurreducens* to the container,
   wherein reduced graphene oxide is produced a period of time after both the graphene oxide and the *Geobacter sulfurreducens* active bacteria are added to the container, by an interaction of the *Geobacter sulfurreducens* and the graphene oxide.

6. The method of claim 5, wherein the *Geobacter sulfurreducens* comprises a strain selected from the group consisting of KN400 and Pili mutant of KN400.

7. The method of claim 5, wherein the *Geobacter sulfurreducens* and the reduced graphene include both metal and non-metal elements.

8. The method of claim 5, wherein elemental doping of reduced graphene oxide occurs simultaneously with the production of the reduced graphene oxide.

9. The method of claim 5, wherein the reduced graphene oxide is produced without toxic precursors.

10. The method of claim 5, wherein the reduced graphene is produced at ambient conditions during the period of time.

11. The method of claim 10, wherein the reduced graphene is produced at 30° C. and atmospheric pressure.

12. The method of claim 5, further comprising: adding electrically active bacteria growth media to the container.

13. The method of claim 12, wherein the electrically active bacteria growth media includes, as an electron donor substrate, at least one of acetate, formate, hydrogen gas, and volatile fatty acids.

14. The method of claim 12, wherein the *Geobacter sulfurreducens* is added to the container after adding the graphene oxide and the electrically active growth media to the container.

15. The method of claim 12, wherein the electrically active bacteria growth media includes an electron donor but not an electron acceptor.

16. The method of claim 15, wherein the graphene oxide acts as the electron receptor.

17. A composition of matter, comprising: reduced graphene oxide; and electrically active bacteria, wherein the composition of matter includes iron oxide and sulfur nanoparticles.

18. The composition of matter of claim 17, comprising *Geobacter sulfurreducens*.

* * * * *